(12) United States Patent
Chalk

(10) Patent No.: US 6,290,910 B1
(45) Date of Patent: Sep. 18, 2001

(54) CONTINUOUSLY VARIABLE VOLUME CHAMBER FOR FLOW INJECTION ANALYSIS

(75) Inventor: Stuart Chalk, Jacksonville, FL (US)

(73) Assignee: University of North Florida, Jacksonville, FL (US)

( * ) Notice: Subject to any disclaimer, the term of this patent is extended or adjusted under 35 U.S.C. 154(b) by 0 days.

(21) Appl. No.: 09/261,911

(22) Filed: Mar. 3, 1999

(51) Int. Cl.[7] ................................................. G01N 35/08
(52) U.S. Cl. ................................................. 422/81; 422/82
(58) Field of Search ............................... 436/50, 52, 139, 436/164, 166, 171, 180; 422/81, 82

(56) References Cited

U.S. PATENT DOCUMENTS

| | | | |
|---|---|---|---|
| 4,639,354 | * | 1/1987 | Bischoff et al. . |
| 4,684,456 | * | 8/1987 | Van Driesen et al. . |
| 4,798,803 | * | 1/1989 | Wolcott et al. . |
| 4,999,305 | * | 3/1991 | Wolcott et al. . |
| 5,045,284 | * | 9/1991 | Smith et al. . |
| 5,434,084 | * | 7/1995 | Burgess, Jr. . |
| 5,604,132 | * | 2/1997 | Capuano et al. . |
| 5,624,846 | * | 4/1997 | Hayashibe et al. . |
| 5,644,395 | * | 7/1997 | Folta . |
| 5,707,868 | * | 1/1998 | Boulay et al. . |
| 5,759,395 | * | 6/1998 | Hagerlid . |
| 6,027,650 | * | 2/2000 | Van Reis et al. . |

* cited by examiner

Primary Examiner—Jill Warden
Assistant Examiner—Brian J. Sines
(74) Attorney, Agent, or Firm—Thomas C. Saitta

(57) ABSTRACT

A method of and apparatus for flow injection analysis using a reaction chamber having a continuously variable volume, where the volume of the reaction chamber may be varied before, during or after introduction of an analyte solution and reagent solution into the reaction chamber. A microprocessor may be incorporated to control the volume of the reaction chamber and other components, either in a preprogrammed manner or in response to particular data measured by a detection device.

8 Claims, 2 Drawing Sheets

CONTINUOUSLY VARIABLE VOLUME CHAMBER FOR FLOW INJECTION ANALYSIS

BACKGROUND OF THE INVENTION

The invention relates to an improved method of flow injection analysis and an apparatus for performing such analysis. More particularly, the invention involves a mixing chamber which is continuously variable in volume, where the volume of the chamber can be increased or decreased before, during or after the mixing or reaction step of flow injection analysis and where the volume change may be controlled by computer in response to analysis results to modify the analysis parameters for optimum desired results.

Quantitative analysis of chemical reactions, where an analyte solution is mixed with a reagent or carrier solution, is a useful tool in many disciplines, including the clinical, agricultural, pharmaceutical, environmental, chemical and medical fields. Various optical detection devices, such as spectrophotometers, fluorescence detectors, luminescence detectors, atomic absorption detectors, and electrochemical detection devices, such as devices to measure potential, voltage, charge or amperage, or any device which can measure either directly or indirectly a chemical or physical parameter of a chemical entity (i.e., the product or reaction result) are useful in providing important information regarding the analyte or the reaction product. It is scientifically beneficial to be able to successively test a number of such reaction samples under identical conditions in order to reduce sampling error. A basic technique to perform this repetitive analysis is through batch analysis, where multiple individual containers are used and the analyte and reagents are mixed in each container under identical conditions. This basic technique can be relatively slow, and requires the handling and cleaning of the many containers.

Since in many situations a large number of analyses of a given reaction are desirable, two techniques have been developed which provide for continuous analysis rather than discontinuous batch analysis of reactions between analytes and reagents. The first is known as continuous flow analysis (CFA) and the second is known as flow injection analysis (FIA). Each utilizes a tube as a conduit through which serial, successive samples are supplied, mixed and analyzed in a continuous process. In CFA, air bubbles are used to separate successive samples so that unwanted intermixing of adjacent samples is precluded. Mixing of the analyte and reagent to produce a reaction product sample for analysis is usually accomplished by providing a relatively long length of coiled tubing through which the samples pass, with mixing of the reagent and analyte occurring as a result of laminar flow, turbulent flow and/or diffusion effects from the tube walls and the action of the air bubbles. The individual samples are part of a continuously moving stream passing through the mixing and analytical apparatus, such that analysis of a large number of samples can be accomplished in reduced time. The FIA method is an improvement over the CFA method, in that the samples within the tube are not separated by air bubbles. Instead the reagent is provided as a continuous carrier solution pumped through the tube, with the analyte injected or introduced into the carrier fluid through a valving mechanism at spaced intervals prior to the mixing coil, with mixing and reaction of the analyte and reagent occurring primarily in the mixing coil. Typical mixing coils are composed of small internal diameter tubes, conventionally about 0.8 mm i.d., formed of Teflon or similar material, in lengths ranging from 0.5 to 4 meters, representing 0.25 to 2 mL in volume. The length and internal diameter of the tube, along with the flow rate, determines the amount and time for mixing and reaction prior to the sample reaching the detector apparatus. Mixing results from laminar flow effects due to transport of liquid in the cylindrical tube and diffusion effects due to the differential in concentration of the analyte and the reagent. Alternatively, the continuously supplied carrier solution may be an inert or neutral solution with both the reagent and the analyte introduced into the carrier stream prior to the mixing coil. With FIA, the equipment involved is simpler since there is no need to supply air bubbles to separate the samples.

While much research has gone into developing mixing and reaction chambers or devices with particular configurations to optimize sample peak height or sample throughput, i.e., peak width, for the particular analysis being performed, a limitation of batch, CFA and FIA methods is that the container, mixing coil or other mixing or reactor device is of fixed volume. This greatly limits the adaptability of the chosen analytical configuration. To vary the mixing volume, different containers must be substituted in the batch method and tubing of different lengths or different internal sizing must be substituted in the CFA and FIA methods—requiring stoppage of the analysis and manual disassembly and reassembly of the equipment. In many situations it is necessary or very desirable to experimentally determine the optimum mixing and reaction parameters for a given type of sample or for the particular detection analysis being performed on the sample, and the availability of a limited number of fixed volume containers or mixing coils limits the ability to obtain the optimum conditions, as well as requiring time consuming trial-and-error to find the best conditions. Obviously, this also requires the physical presence of a researcher to make the changes, such that altering the equipment remotely or by computer is impossible. A related limitation of the known analysis methods and equipment is that the volume of the mixer/reactor cannot be altered during the mixing/reaction step itself, that is, while the analyte and reagent are combining within the mixer/reactor.

Among other objects which will be apparent from the detailed disclosure to follow, it is an object of this invention to provide an improved method of continuous flow or flow injection analysis and a novel apparatus for performing this method wherein the volume of the mixing and reacting chamber is continuously variable such that any desired volume within the maximum and minimum volume limits of the system can be chosen, and such that the volume of the mixing and reacting chamber may be altered while the analyte and reagent are mixing and reacting. It is a further object to provide such a method and apparatus which may be controlled by a computer or microprocessor, or by remote signal, either in a predetermined manner or in response to the analytical data detected during an analysis run, such that variation in volume of the mixing and reaction chamber is automatic or based on the results of prior analytical runs. It is a further object to provide such a method and apparatus where individual or multiple signal or peak attributes for a sample for a particular detector device, such as shape, height, or width of a detected peak pattern, can be controlled and modified as desired, where change in volume does not require disassembly and reassembly of components of the system, where the volume of the mixing and reaction chamber can be static or dynamic during analysis, and where the analysis can be performed remotely with no requirement for the physical presence or interaction of a researcher or technician.

SUMMARY OF THE INVENTION

The invention comprises in general a method of flow injection analysis where the volume of the reaction chamber in which the mixing of the analyte and reagent primarily occurs is variable, and the apparatus which enables the volume of the reaction chamber to vary. The flow injection analysis system comprises standard means to continuously supply successive, serial samples of an analyte and reagent mixture through the reaction chamber and a detector means for measuring specific characteristics of the reaction of the analyte and reagent, where the reagent solution itself or a separate inert solution acts as a carrier. The detector means for providing specific data may comprise any type of analytical equipment, including but not limited to optical detection devices such as spectrophotometers, fluorescence detectors, luminescence detectors, atomic absorption detectors, and electrochemical detection devices such as devices to measure potential, voltage, charge or amperage. In a preferred embodiment of the invention, the reaction chamber is formed by the combination of a piston capable of movement in a reciprocating manner mated within a fixed main body, such that translation of the piston relative to the main body enlarges or diminishes the volume of the reaction chamber. Preferably the piston is moved by a motor or other powered means, although it may be manually operated, and most preferably the variation in volume of the reaction chamber is controlled by a microprocessor. This enables the volume of the reaction chamber to be adjusted at predetermined intervals between samples or during the mixing/reaction process itself in a predetermined manner. This also enables the reaction chamber volume to be adjusted in response to data received by the microprocessor from the detector means. In this manner the signal characteristics of the reaction between the analyte and the reagent produced by the detection device, such as peak height, width, or shape, can be adjusted as desired. Use of the microprocessor also allows the flow injection analysis to be performed without requiring a technician to be present as all other components of the system can be under computer control.

DETAILED DESCRIPTION OF THE INVENTION

With reference to the drawings, the invention will now be described in detail with regard for the best mode and the preferred embodiment. In general, the invention is an improved method and apparatus for performing flow injection analysis (FIA) of reaction samples, where the combination mixing and reaction means, wherein the analyte (the solution about which information is sought) and reagent (the solution which reacts with the analyte to produce a reaction product which is subsequently analyzed or measured by one or more detector means) combine to produce a reaction sample or product for analysis, is a reaction chamber having a volume which is variable in a continuous or indexed manner between and maximum and minimum volume, either before, during or after the mixing and reaction process.

Figure 1:
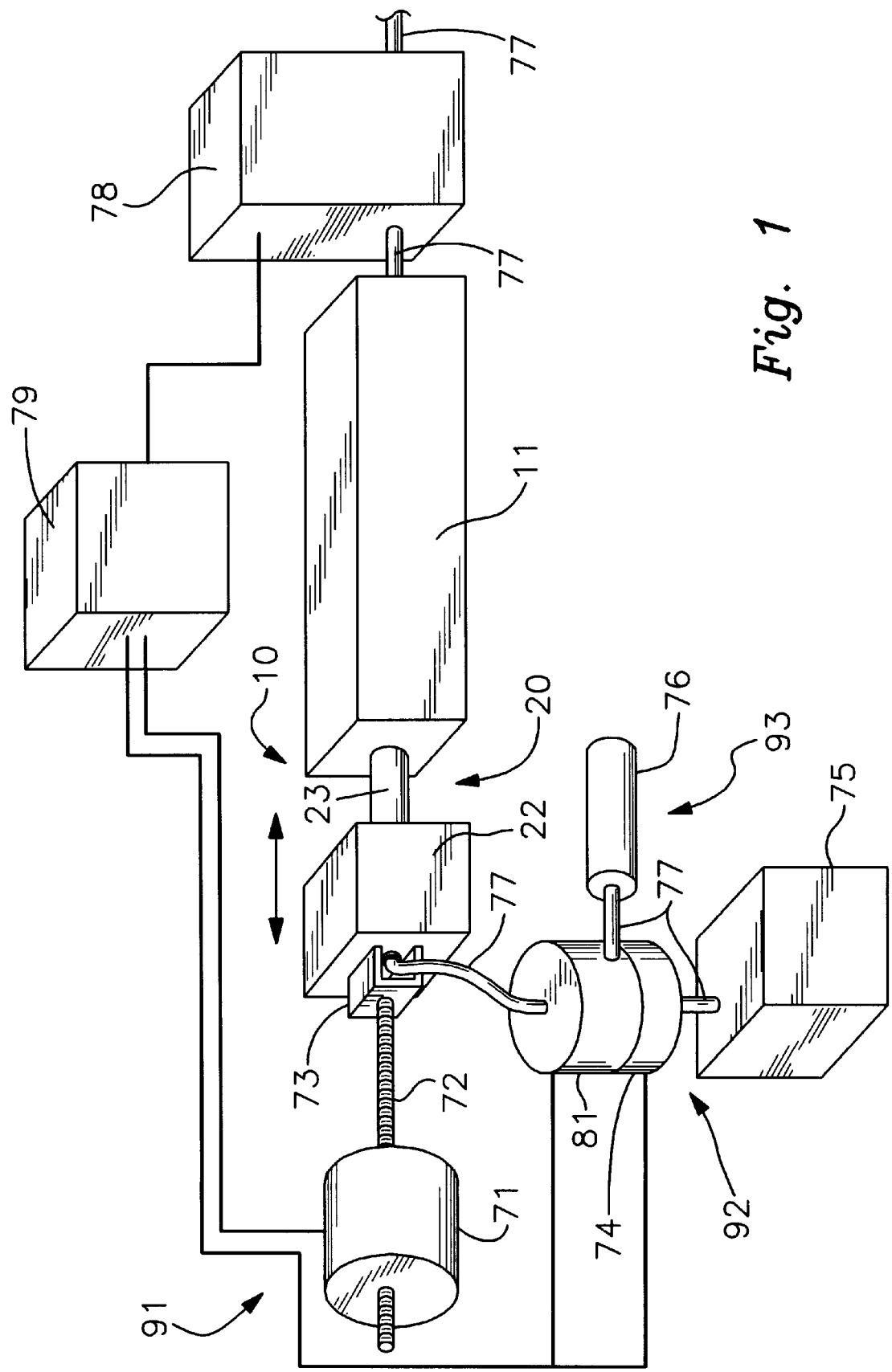
FIG. 1 is representational view of the components of the flow injection analysis system.

The components of the FIA system of the invention are shown in FIG. 1. The FIA process involves means 92 to provide a continuous flow of reagent or carrier solution, which as shown in the drawing is a reagent solution retrieved from the reagent/carrier solution reservoir 75 and passed through conduits 77 by pump means 74 through a reactor device 10 and detector means 78. Means 93 to introduce an analyte solution at desired intervals into the continuous reagent or carrier stream includes an analyte reservoir 76, with the introduction of the analyte into the reagent stream occurring in any of the known manners in FIA, which as drawn incorporates a valving means 81 such as for example a six port rotary valve. Detector means 78 may comprises any analytical, detection or measuring device or apparatus which can measure either directly or indirectly a chemical or physical parameter of a chemical entity, product or reaction result, such as for example optical detection devices such as spectrophotometers, fluorescence detectors, luminescence detectors, atomic adsorption detectors, and electrochemical detection devices such as devices to measure potential, voltage or amperage. Detector means 78 may be a separate component in the system, or may be incorporated directly into the reactor 10 to directly analyze the reaction results as produced in the reaction chamber 12. Alternatively, the reagent solution may be provided from a separate reagent reservoir and introduced into a carrier stream of an inert, neutral or non-reactive solution by separate valving means, with reservoir 75 containing the carrier solution only. Such systems, including the pump means 74, valving means 81, reservoirs 75 and 76, and detector means 78 are well known in the FIA art, and equivalents and substitutions to these components known in the art are incorporated by reference herein.

Figure 2:
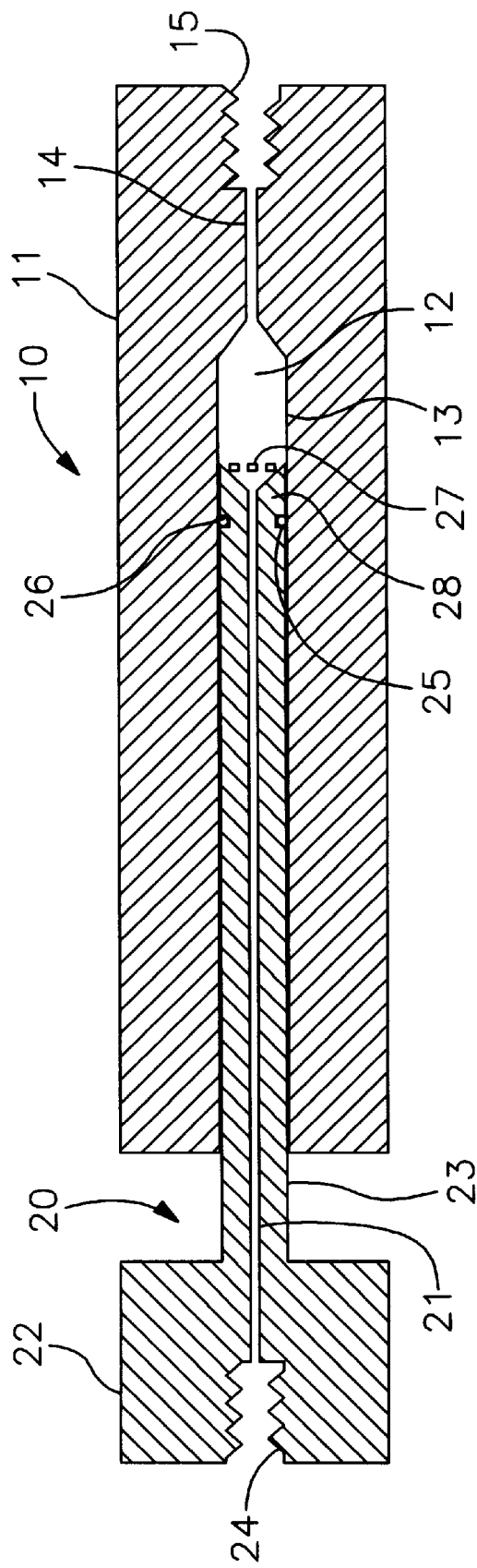
FIG. 2 is a cross-sectional view of the continuous variable volume reactor, showing the main body and piston as defining the reaction chamber.

Reactor means 10 and the components which interact with reactor means 10 define the unique aspects of the invention, as reactor means 10 enables the FIA system to be utilized in novel ways precluded by the former known systems. As seen in FIG. 2, reactor means 10 comprises a main body or cylinder 11 having a piston receiving bore 13, an outflow bore 14 connected to the reaction chamber 12 partially defined by said piston receiving bore 13, and preferably a connector means 15 for easy connection of conduit 77 for passage of the reaction product from the reactor 10 to the detector means 78. Reactor means 10 further comprises a piston 20 capable of movement in a reciprocating manner which moves axially within piston receiving bore 13, the piston 20 having a head 22 and an elongated cylinder portion 23 which is sized to fit within the piston receiving bore 13 of the main body 11. Piston 20 further comprises an internal inflow bore 21 which extends to the free end 28 of cylinder 23, and preferably connector means 24 for easy connection of conduit 77 from the pump means 74 or valving means 81. An annular O-ring channel 25 to receive O-ring 26 is positioned near the free end 28 to prevent loss of solution around the cylinder 23. The position within the piston receiving bore 13 of the free end 28 of piston 20 determines the actual volume of the reaction chamber 12. If the piston 20 is withdrawn relative to the main body 11, the volume of the reaction chamber 12 is increased. If the piston 20 is inserted relative to the main body 11, the volume of the reaction chamber 12 decreases. In an alternative embodiment, the inflow bore 21 may be directed into the wall of the reaction chamber 12 rather than internally through the piston 20.

Figure 3:
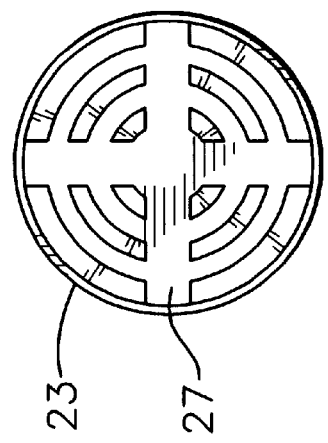
FIG. 3 is an axial view of a baffle positioned on the internal end of the piston.

The volume of the reaction chamber 12 is continuously variable over a range between the maximum and minimum volumes dictated by the size of the piston receiving bore 13. The volume may be changed in either a continual or incremental manner. While a minimal mount of mixing and reaction between the analyte and the reagent will occur within the conduit 77 and the inflow bore 21 of piston 20, the primary locus of mixing and reaction is the reaction chamber 12. To increase mixing, grids or baffle means 27, as shown in FIG. 3, may be provided at the free end 28 of cylinder 23. Likewise, the configuration of the free end 28 of the piston cylinder 23 may be altered from that shown to increase mixing. Furthermore, other static or non-static mixing means may be incorporated into the reaction chamber 12 to increase mixing, such as by providing magnetic stirrers or ultrasound sources.

While translational motion of piston 20 relative to main body 11 may be performed manually, it is preferred that some power means 91 to vary the volume of the reaction chamber 12 be provided, such as motor 71 having a threaded rod 72 connected to piston head 22 by bracket means 73, the motor 71 being of the type capable of advancing or retracting threaded rod 72, and thus advancing or retracting piston 20. Other suitable mechanisms may be substituted for means 91, such as hydraulic, pneumatic or geared mechanisms. The system may be remotely operated through electrical, radio, infrared or other signals. It is most preferred that volume varying means 91, and optionally other operational components of the system, be controlled by a microprocessor means 79. This enables the variation in volume of reaction chamber 12 to be precisely controlled and the changes in volume may be patterned or otherwise predetermined, such that physical intervention or presence of a technician is not required. In addition, the microprocessor means 79 is preferably structured to be in communication with detector means 78, such that microprocessor means 79 can be programmed to vary the volume of reaction chamber 12 in response to data produced by analysis of prior reaction product samples by detector means 78. In addition, where the mixing and reaction time is sufficiently long, the microprocessor means 79 can be programmed to vary the volume of reaction chamber 12 while the process steps of mixing, reaction and measurement of a reaction product are occurring, in response to data produced by the detector means 78.

By providing a system as described above with a variable volume reaction chamber 12, and especially with a system incorporating a microprocessor means 79, the methodology of FIA can be expanded beyond the typical analyses performed with static volume mixing chambers. At a basis level, the variable volume reaction chamber 12 allows the volume of the reaction chamber 12 to be altered between reaction product samples without requiring disassembly and reassembly of the FIA system. More importantly, the new system allows the volume of the reaction chamber 12 to be varied during the actual mixing and reaction process, either in a continual manner, a step-wise manner or any chosen combination of volume variation. Thus the concentration of the reaction product can be controlled to produce optimized or variable analytical results for comparison purposes. For example, peak shape, height or width can be manipulated by varying the volume of the reaction chamber 12 during the reaction process, or successive analyses can be made with each analysis performed in a different volume to determine optimum sampling conditions. With microprocessor means 79, the system can be programmed to vary the volume of the reaction chamber 12 automatically in response to a predetermined schedule, or to vary the volume of the reaction chamber 12 in response to data which is received from the detector means 78. This allows the system to automatically optimize the sampling conditions and to respond to changes in the reaction results.

It is contemplated that equivalents and substitutions to certain elements set forth above may be obvious to those skilled in the art, and the true scope and definition of the invention therefore is to be as set forth in the following claims.

I claim:

1. A system for performing flow injection analysis of the reaction product of an analyte solution reacting with a reagent solution, the system comprising:

mixing means to mix an analyte solution and reagent solution to create a reaction product for analysis, said mixing means comprising a reaction chamber having a variable volume, where the mixing of said analyte solution and said reagent solution occurs primarily within said reaction chamber, means to vary the volume of said reaction chamber when said analyte solution and said reagent solution are in said reaction chamber, detector means to measure the reaction product, and pump means to provide continuous flow of successive samples of mixed analyte and reagent serially through said mixing means and said detector means.

2. The system of claim 1, where the volume of said reaction chamber ranges from a maximum volume to a minimum volume, and where said volume is variable in a continuous manner.

3. The system of claim 1, where said mixing means comprises a reactor main body which receives a piston where relative movement between said piston and said main body determines the volume of the reaction chamber.

4. The system of claim 3, where said means to vary the volume of said reaction chamber comprises means to move said piston while said main body remains fixed.

5. The system of claim 1, further comprising microprocessor means to control said means to vary the volume of said reaction chamber.

6. The system of claim 5, where said microprocessor means controls said means to vary the volume of said reaction chamber in response to data received from said detector means.

7. The system of claim 1, further comprising a reagent reservoir and an analyte reservoir, where said pump means draws said reagent solution from said reagent solution reservoir.

8. The system of claim 7, further comprising means to introduce said analyte solution into said reagent solution.

* * * * *